United States Patent [19]

McNally et al.

[11] 4,080,966
[45] Mar. 28, 1978

[54] AUTOMATED INFUSION APPARATUS FOR BLOOD PRESSURE CONTROL AND METHOD

[75] Inventors: Robert T. McNally, Secane, Pa.; Karl Engelman, Cherry Hill, N.J.; Abraham Noordergraaf, Haverford, Pa.

[73] Assignee: Trustees of the University of Pennsylvania, Philadelphia, Pa.

[21] Appl. No.: 713,645

[22] Filed: Aug. 12, 1976

[51] Int. Cl.² .............................................. A61M 5/14
[52] U.S. Cl. .......................... 128/214 E; 128/2.05 D; 128/214 F; 128/DIG. 13
[58] Field of Search .......... 128/2.05 D, 214 E, 214 F, 128/DIG. 12, DIG. 13, 213, 227

[56] References Cited

U.S. PATENT DOCUMENTS

| | | | |
|---|---|---|---|
| 2,690,178 | 9/1954 | Bickford | 128/213 |
| 3,143,111 | 8/1964 | Green | 128/213 |
| 3,163,176 | 12/1964 | Darling | 128/214 E X |
| 3,319,623 | 5/1967 | London | 128/214 E X |
| 3,651,806 | 3/1972 | Hirshberg | 128/214 E |
| 3,938,506 | 2/1976 | Birnbaum et al. | 128/2.05 D X |

Primary Examiner—Dalton L. Truluck
Attorney, Agent, or Firm—Paul & Paul

[57] ABSTRACT

A reliable and inexpensive method has been developed to continually regulate the blood pressure of mammals at virtually any desired level. The pressure thus regulated may be maintained within 10 mm Hg tolerances. The method may be carried out by a closed loop apparatus with which (1) the actual blood pressure is continually measured, (2) a function of the actual blood pressure is compared with a desired blood pressure, (3) any difference between the blood pressure expressed by the function of the actual blood pressure and the desired blood pressure is converted into an error signal, (4) the error signal is converted into proportional and derivative functions which in turn (5) control the rate of pumping of a supply of a liquid hypertensive agent or a hypotensive agent into the circulatory system of the mammal.

10 Claims, 4 Drawing Figures

PRIOR ART

AUTOMATED INFUSION APPARATUS FOR BLOOD PRESSURE CONTROL AND METHOD

BACKGROUND OF THE INVENTION

This invention relates to the regulation of blood pressure, and particularly to apparatus and methods for the continuous regulation of blood pressure by controlled infusion of drugs which combat hypertension and hypotension.

Several drugs are known and commercially available which when administered in proper dosages have the primary effect of regulating the blood pressure. As is set forth in greater detail hereinafter, such drugs may be used either to alter cardiac output (either by changing the capacity of the heart or intravascular volume), or to alter peripheral resistance or state of contraction of the arteriolar resistance vessels. Hypotensive agents act by reducing one or several of these parameters, and hypertensive agents result in opposite effects. In either event, the rate of onset and degree of effectiveness of drugs to achieve satisfactory pressure levels is substantially dependent upon the mode of administration and pharmacodynamics of the drug used.

Conventionally, drugs for the regulation of blood pressure are administered by continuous intravenous drip or pump, intramuscular or intravenous injection, or orally. All such methods, however, involve severe difficulties in controlling undesired rise and decay of drug concentration within the patient, which changes may be exponential in character.

It is a primary object of the present invention to provide apparatus and methods for automatically, safely, and effectively providing acute continuous blood pressure regulation through the controlled infusion of drugs.

A major class of systems attempting to achieve automated continuous control involves utilization of a computer to assume select aspects of the decision process. In such systems, a large number of measured parameters from the subject are processed logically, with the ultimate result being a decision whether and how much further infusion of drugs is presently required. Some such prior art systems are open loop and others are closed loop in function, and some work on fixed periodicity in digital fashion, while others work continuously in analog fashion. For example, in one system described by M. Schade in Technical Report 6972-2 of the Stanford University Center for Systems Research, August 1971, a computer, controller, pump, and subject with blood pressure information feedback operate independently from any manual intervention. In Schade's system, the actual blood pressure of the subject is compared with a desired pressure, and the resulting error signal is manipulated by a computer controller which models behavior of the subject and which activates a pump to infuse the appropriate amount of drug. At one point (p. 53), Schade suggests that an adaptive differential-model controller might be useful, but also notes that such an approach involves at least one weakness in that one must consider derivatives to form the model.

While interactive computer control involves extensive capacity for monitoring plural data from the subject, and multiple effects of the infused drug, such systems are unduly large, complex, and expensive for general availability. It is accordingly an object of the present invention to provide relatively simple and economical systems for the infusion of drugs to control blood pressure.

In a second class of prior art systems, fixed logic controls the rate of infusion of a blood pressure control drug in response to an error between the present pressure and a desired pressure. In one exemplary machine, as described by H. Muller and M. Stuach in Zeitsch. Biol. 116:288-290, 1969, a hypotensive state was established by infusion of phentolamine, and the blood pressure was then raised, based on proportional plus integral control, by infusion of epinephrine. In another example, commercially available Harvard Apparatus Servo Controlled Liquid Pumping System, Model 990, Millis, Mass., which is discussed in greater detail hereinafter, the error between present and desired pressure is manipulated by a proportionality factor, whereupon a pump is operated to alter infusion rates. Both of the foregoing examples in the latter class involve serious deficiencies. In the former, the pressure reduction-increase procedure tends to involve steady state errors, and furthermore tends to be quite slow to respond. In the latter case, the degree of control achieved is inadequate, with resultant variation and overshoot in pressure.

It is accordingly a further object of the present invention to provide closed loop control whereby the blood pressure is brought to the desired level speedily and without substantial danger of overshoot of the desired level.

SUMMARY OF THE INVENTION

The present invention involves apparatus and methods for the control of blood pressure utilizing controlled infusion of drugs in an effective, speedy, and safe closed loop fashion. A desired arterial blood pressure level is established for the subject, and the present blood pressure is monitored. Rather than basing control on the phasic arterial pressure which thereby introduces a degree of inaccuracy to the control process, the measured pressures are filtered, advantageously by integration, to evaluate mean arterial blood pressure. It is this mean value which is compared with the desired mean arterial pressure level, generated by a constant voltage source thereby yielding an error signal upon which control is based. Advantageously, the error signal is manipulated by proportional control, and further its time rate of change (i.e., the derivative of the rate of change in the error signal) is evaluated, scaled, and combined with the proportional control signal. This combination in turn, operates a pump under desired constraints, whereby the blood pressure of the patient is brought within desired ranges.

Clinical and experimental uses of embodiments of the present invention demonstrate high reliability and excellent performance in a relatively simple and inexpensive system. Filtering of the phasic measured blood pressure, and control on the basis of mean arterial pressure, substantially improves the control process, and proportional plus derivative (plus integral) control substantially eliminates overshoot or steady state error of the desired pressure level. The rate of response is rapid, thereby minimizing the duration of undesirable blood pressure levels.

DETAILED DESCRIPTION

Figure 1:
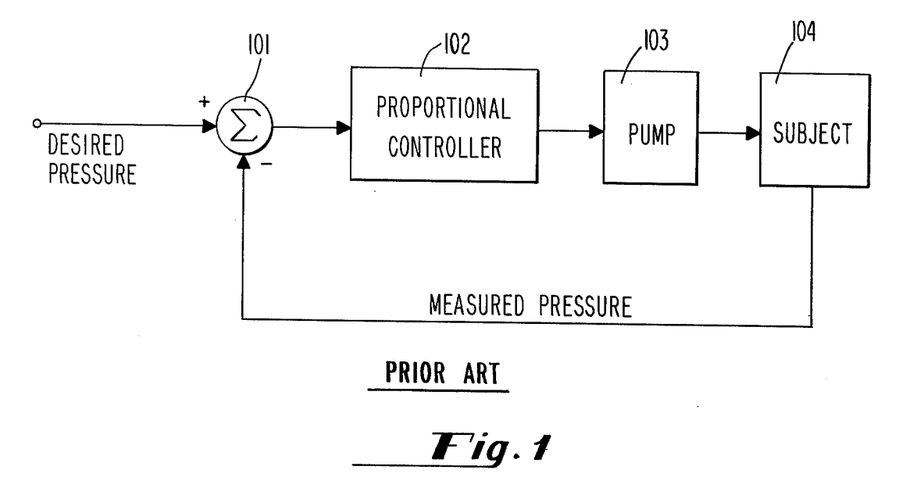
FIG. 1 shows a block diagram of a prior art system upon which the apparatus of the present invention is designed to improve.

As set forth hereinbefore, many of the relevant prior systems known to the inventors hereof concern extensive and complicated computer control, with its attendant difficulties of increased cost and lack of general availability. Probably because of the critical parameters of the infusion control process, few non-computerized systems have been developed, and these are understood to involve substantial difficulties. FIG. 1 shows a block diagram representation of a typical non-computerized control system. In FIG. 1, the measured blood pressure from a subject indicated at 104, is coupled back and compared at 101 with a desired, or reference blood pressure. The comparison at 101 may be done, for example, by subtraction. The differential between the desired and measured pressure is coupled to a controller, which produces a scaled control signal based on proportional processing of the error between desired and measured pressures. This proportional control signal operates a pump 103, which in turn infuses the appropriate drug into the subject.

Typically, the pump 103 is gear driven with a servo motor capable of responding from 0 to a given maximum speed, depending upon the amplitude of the generated control signal, which in turn is proportional to the error signal.

Systems of the sort referred to in FIG. 1 involve some basic difficulties. First, the measured pressure from the subject is phasic, on a cycle of 60-100 per minute (reflecting the heart rate) which results in very rapid alternating polarity of pumping in accordance with the phasic input. At steady state this may result in reversal of pump direction with net withdrawal of fluids (blood). If the reverse polarity is eliminated a net forward movement in pumping, due to momentum, may result in a continued infusion of drug, even if not required for steady state control. Without appropriate anticipatory controls, the time delay in biological systems between infusion and onset of action of drug may result in an excessive dose of drug being infused prior to sensing drug effect, thus yielding wide swings of drug response with excessive (potentially dangerous) overshoots. The incorporation of proportional control, alone, in the system pictured in FIG. 1 is inadequate to prevent such oscillations.

Figure 2:
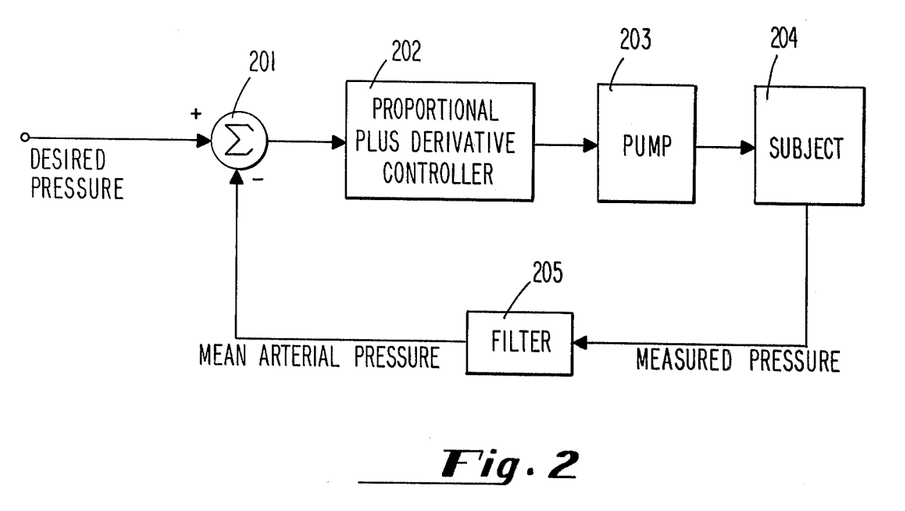
FIG. 2 shows a block diagram of an illustrative embodiment of the apparatus of the present invention.

FIG. 2 depicts a block diagram embodiment of the present invention in a form similar to that of the prior art system of FIG. 1. In FIG. 2, the blood pressure of a subject indicated at 204, is measured in conventional fashion, but is not used directly for control. Rather, the measured pressure is filtered at 205, preferably by integration, to yield mean arterial pressure. Use of the filter 205 eliminates the phasic aspect of the measured pressure, thereby giving a more stable representation of the subject's condition for the purposes of control. The mean arterial pressure is compared with a desired mean arterial pressure at 201, for example by subtraction, thereby producing an error signal. The error signal is coupled to a controller 202, which in preferred form involves proportional and derivative control aspects. Integral control may also be advantageously added to the controller 202. As the error signal from comparator 201 is evaluated at the controller 202, a control signal is synthesized for operation of a pump 203, which infuses drug into the subject in response to the control signal.

In FIG. 2, the proportional control aspect of controller 202 performs the major control function in that larger error signals are better compensated by proportional control, as in the prior art. However, since biological systems usually incorporate some time delay, proportional control, alone, is simply inadequate. In FIG. 2, derivative control is used in controller 202 to anticipate required changes, such as the rapid changes in pressure which would lead proportional controllers to overshoot the desired pressure. Then, if offsets further result, integral control may be incorporated for purposes of correcting the offset.

As in the prior art, proportional control involves multiplying the error signal by a given factor, represented herein as "A", to yield a component of the control signal which is directly proportional to the error signal. The derivative aspect of the controller 202 involves evaluation of the time rate of change of the error signal, which also may be manipulated by a scaling factor, represented herein as "B". The two control aspects are combined at 202 by addition, to yield the control voltage for the pump 203. That is Error = Desired pres. − mean arterial pres.

$$\text{Control} = A \times \text{error} + B \times \frac{d(\text{error})}{dt}$$

For the embodiments set forth herein, the pumps for infusing the control drug into the subject advantageously are embodied as those commercially available under the title "Harvard Model 1991 Infusion Pump", available from the Harvard Apparatus Company, Millis, Massachusetts. Suggested circuitry for the other apparatus is presented in FIG. 3, and it is anticipated that numerous other embodiments of the specific circuitry which meet the spirit and scope of the present invention will occur to those skilled in the art.

The operation of the FIG. 2 embodiment may be appreciated by consideration of certain operational circumstances. The following four conditions are set forth for a hypertensive subject with exactly the opposite polarities being involved for hypotension. Basically, these four conditions characterize the circumstances during which control will be needed.

First, the mean arterial pressure (i.e., "MAP") may be at a level above the desired and there exists a large error to activate the pump. However, as the pressure approaches the desired level, this error signal diminishes and decreases the proportional control signal. The derivative will also sense the rate of error change and will slow the approach to the desired level by further reducing the signal to the pump. Very rapid pressure reductions creating correspondingly rapid error changes will result in a large derivative and will decrease even further the pumping to the point where drug infusion may stop before the desired level is achieved. This anticipates the delayed reduction in pressure attendant upon the amount of drug that has already been infused but which has not reached the receptor sites and produced a pharmacologic effect. For the second case, an overshoot, the error and its derivative are positive and no pumping is allowed by the system. In the third condition the pressure begins to rise, the error is still positive, but the derivative signal is negative. If the rise is slow, the output of the pump will remain positive and no pumping will result; however, if there is a rapid change in pressure, the voltage to the pump may change sign and pumping will commence in order to prevent a return to a level above the desired. Finally, in the fourth case, characterized by a steady state error above the desired, both the proportional and derivative signals are negative and pumping will proceed.

As set forth above, the foregoing four situations are presented for a hypertensive subject. If the apparatus is being used to control hypotension, mere reversal of index voltages will bring about the desired operation.

Figure 3:
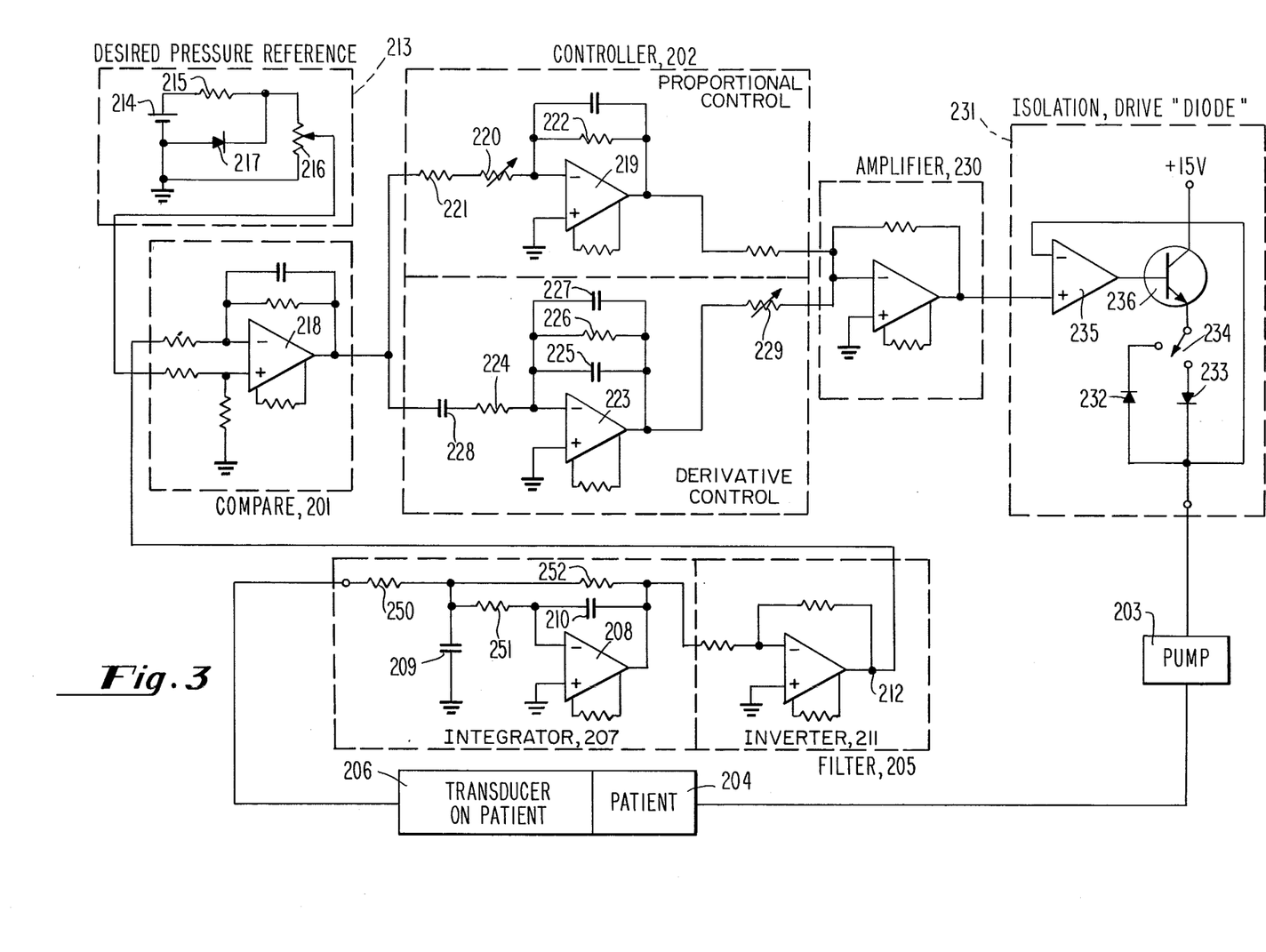
FIG. 3 shows a detailed schematic of the embodiment of FIG. 2.

FIG. 3 shows a schematic diagram of a preferred detail of the embodiment of FIG. 2. In FIG. 3, the patient is represented at 204, with a blood pressure transducer 206 affixed appropriately thereon. The transducer 206 senses the actual blood pressure of the subject, and converts it to a voltage of a proportional amplitude, which may vary within a selected range corresponding to the blood pressure of the patient. Many such transducers are readily available commercially.

As set forth hereinbefore, the measured blood pressure from the transducer 206 is filtered at 205 prior to comparison with the desired reference. In the preferred embodiment of FIG. 3, the filtering occurs by means of integration, utilizing an active low-pass filter as shown. In the integrator 207, an operational amplifier 208 has input and feedback circuity which determines the exact parameters of the filter. In particular, capacitor 209 regulates the high frequency cutoff, and capacitor 210 determines rolloff capabilities. If each of the resistors 250 through 252 of integrator 207 are 11.8 K ohm, capacitor 209 is 300 mf., and capacitor 210 is 33 mf., a phasic blood pressure of 1 Hz would be attenuated starting at 0.1 Hz, and would be completely filtered by 1 Hz. Since the operation of amplifier 208 produces at its output a signal of inverse polarity to that at its input, the filtered signal is inverted at 211 in conventional fashion, and is coupled to a comparator 201. Hence, the signal presented at output terminal 212 of the inverter 211 represents the mean arterial pressure of the patient.

A desired pressure reference voltage is produced at 213 by dropping the voltage of a zener diode 217 (biased by a supply 214 and a resistor 215), across a resistor 216. The tap on resistor 216 is adjustable for different desired pressures, and is also coupled to the comparator 201.

The comparator 201 is embodied as an operational amplifier 218 having the mean arterial pressure from the inverter 211 coupled to its inverting input, and the desired pressure from reference source 213 coupled to its non-inverting input. The output of comparator 201, which is the error signal upon which control is based, therefore is the difference between the desired pressure and the mean arterial pressure. If the desired pressure is greater than the mean, the error signal is positive, and if the desired pressure is less than the mean, the error signal is negative.

The error is in turn coupled to the controller 202, which involves parallel paths for proportional control and for derivative control. Integral control is obtained simply by adding a third parallel path consisting of an integrator. The proportional control is embodied as an operational amplifier 219 having feedback and input circuitry similar to that of comparator 201, with the positive input connected to ground. An adjustable resistor 220 is placed in the input circuitry of amplifier 219, such that in accordance with the known performance of operational amplifiers, the gain factor, which also is the proportional control factor A, is set by the ratio of the feedback resistance 222 to the input resistance, which is the sum of resistors 221 and 220. Hence, a signal is presented at the output of operational amplifier 219 which is equal to the error signal inverted and multiplied by the factor A.

The derivative control aspect of controller 202 is embodied in a path parallel to the proportional control, and centering about yet another operational amplifier 223. As set forth hereinbefore, the derivative control senses the time rate of change of the error signal, which effectively represents an anticipation of a change in pressure. Therefore, the overall control process is facilitated. Generally, derivative control should be designed to avoid noise generation. Capacitors both in the feedback and input circuitry account for the derivative function. A critical frequency of 25 Hz is obtained if the input capacitor 228 is 1 mf., the input resistor 224 is 6.8K., the feedback capacitor 225 is 1500 pf., and the feedback resistance 226 is 51 M ohm. Noise generation is further reduced if more capacitance is added in feedback by means of capacitor 227 to produce a total feedback capacitance of 83,000 pf. (which changes the critical frequency from 25 Hz to 6.7 Hz, but which is still acceptable). Therefore, the derivative control circuit only responds when there is a change in the error signal, and which is represented by a voltage at the output of amplifier 223. In turn, the amplifier output voltage is scaled by an adjustable output resistor 229, and which corresponds to the derivative scaling factor B.

The control signal components from the proportional and derivative control aspects of the controller 202 are inverted and are combined and scaled appropriately by an amplifier 230, which for preferred embodiments scales the control signal to a range of $\pm$ 1 volt pursuant to specifications on the pump 203. Further, in order to prevent an inverse polarity and withdrawal pumping of pump 203, a "diode" circuit 231 composed of operational amplifier 235 and transistor 236 is provided. In the diode circuit, the isolation function which prevents withdrawal pumping is afforded by oppositely directed diodes 232 and 233 which are selected by a switch 234, thereby providing for pumping based on positive or negative signals, depending whether reduction or increase in blood pressure is the desired action. Thus, diode 231 operates the pump 203 in response to the scaled control signal from amplifier 230, and the drug is appropriately injected into the subject. The control loop is thereby closed.

All amplifiers shown in the FIG. 3 embodiment are conveniently embodied by those commercially known as Analog Devices Model 118, and may also be embodied by a large number of similar commercially available devices.

APPLICATION

Hospitalized hypertensive and hypotensive patients who require immediate and constant blood pressure regulation are usually treated in intensive care units. Here the blood pressure may be regulated by continuous or intermittent intravenous administration of appropriate drugs to maintain the desired level. While current facilities usually provide sophisticated monitoring equipment to document the patient's vital signs, the administration and adjustment of the drugs is often haphazard, erratic, or inexact.

It is an object of this invention to facilitate this procedure through automated means which would ensure uniform control and allow professional staff to better monitor and care for the patient without the need to perform constant manual manipulation of drug infusion.

Since the regulation of blood pressure may be thought of as a function of pump action (cardiac output) and system resistance to flow (peripheral arterial resistance), alteration of either of these modalities will result in changes of pressure in a predictable direction. The cardiac output is a function of two variables; the capacity of the pump (cardiac function) and the availability of blood to be pumped (venous return and intravascular volume). The latter may be directly affected by infusion or withdrawal of blood or fluids, but this is a cumbersome and impractical approach in biological systems unless there is a manifest deficiency of fluid volume. Likewise, drugs which primarily affect cardiac function are usually undesirable unless very special circumstances pertain. Thus, the usual mode of altering blood pressure, especially reduction of undesirably high blood pressure is through the use of pharmacologic agents which act primarily to alter the state of contraction of the arteriolar resistance vessels, though some drugs used for this purpose may also have lesser secondary effects on the heart.

The time course and degree of possible control of pharmacological effects depends upon the route of drug administration and the pharmacodynamic characteristics of the drugs employed (oral administration, etc). The use of oral administration of drugs to raise or lower pressure is possible, but the onset of response is usually delayed for several hours or more and acute accurate control is usually unpredictable or impossible. Parenteral administration of drugs by subcutaneous or intramuscular routes suffers from similar shortcomings, though more rapid responses can be achieved via the latter route, especially when appropriate drugs are chosen. Nevertheless, the most rapid and surest method of administering and controlling drug effects is by the intravenous route, especially with agents chosen for rapid onset of action. When this characteristic is coupled with a short drug half-life, the situation is most amenable to timely manipulation of drug administration so as to achieve close control of response. However, the latter circumstance may result in marked vacillation of effect if the control mechanism for drug administration is not capable of rapid and accurate accommodation to changes in circumstances and responses. Thus, the potential advantage of intimate control provided by the intravenous administration of a drug with rapid onset and decline of pharmacologic response is lost if the mode of regulation of drug administration does not share the capacity for constant testing of actual vs. desired response and the capacity to alter drug administration appropriately. For instance, if a vasoconstrictor drug was being infused to raise blood pressure, and the rate of infusion was not appropriately altered after the onset of activity, there could result either an inadequate response which failed to achieve sufficient raising of pressure or an inappropriate overresponse with resultant excessively high blood pressure which could prove injurious or even lethal to the subject. Likewise, if similar defects in control of drug effect resulted from the administration of a vasodilator drug either inadequate or excessive response might result — in the latter instance, shock or death might ensue.

For the purposes of this invention two drugs with rapid pharmacodynamics were chosen since they have manifest clinical utility and an improved method of regulating drug administration rates would be most desirable. For these purposes L-norepinephrine was chosen as the vasopressor and sodium nitroprusside was selected as the agent to lower blood pressure.

EXPERIMENTAL PROCEDURE

All animal studies were performed on dogs (20 kg, mongrel) which had fasted 24 hours prior to the nonsterile surgical procedure. Induction of anesthesia (sodium pentobarbitol, Nembutal, 25 ug $kg^{-1}$), was achieved by percutaneous intravenous injection into the saphenous vein. Ventilation was sustained using a Harvard Ventilator with control settings of 300 cc stroke volume at 12 cycles per minute. Venous catheters were inserted into both femoral veins for drug infusion. An arterial catheter was introduced into one femoral artery for blood pressure monitoring. All catheters were advanced approximately 20cm, and these vessels were ligated distal to the point of catheter insertion. Intraarterial pressure was measured with a Statham P23db transducer, and was recorded on a Honeywell (model 1508-A) oscillographic recorder.

Sodium Nitroprusside (NP), (Nipride R, Hoffman-LaRoche) was reconstituted with 5% dextrose in water to a concentration of 800 ug $ml^{-1}$. L-arterinol bitartrate monohydrate (L-norepinephrine — Sigma Co., NE) was dissolved in 5% dextrose in water to a concentration of 20 ug $ml^{-1}$. Angiotensin II (Hypertensin — CIBA R) was dissolved in sterile distilled water to achieve a final concentration of 20 ug $ml^{-1}$.

Initially studies were carried out to determine whether the Harvard Apparatus Servo Controlled Liquid Pumping System was capable of achieving rapid accurate modification of blood pressure to desired levels. Dogs were infused with NE at constant rates sufficient to raise mean arterial blood pressure to 180–200 mm Hg. Then, while the NE infusion was maintained, the Harvard device was activated to infuse NP with a target objective to reduce the arterial pressure back to the animal's control or spontaneous preinfusion blood pressure, which in all animals ranged between 120–140 mm Hg.

As a result of these experiments it was concluded that the Harvard device was incapable of achieving this result satisfactorily. Among the significant problems observed were marked oscillations of blood pressure with large deviations ($\pm$ 30 mm Hg) above and below the desired level. Unless machine settings were fortuitously picked, these oscillations persisted without significant abatement. On occasion, gradual damping of oscillation was observed over a period of 20–30 minutes. Another undesirable response observed was the function of the device to reverse direction of pumping when blood pressure changes exceeded the desired response. The result was an intermittent withdrawal of blood from the vein with consequent dilution and contamination of the drug contained within the infusion syringe. This aspect of the function of the Harvard device rendered it unusable for animal or clinical purposes.

Therefore, a program was then undertaken to develop a suitable instrument to achieve the stated purpose. Initial studies (Table 1) were performed to document the time constants of onset and decline of the pharmacologic effects of NE and NP. These studies (Table 1, dogs 1-3) consisted of bolus and continuous infusion of NE and NP. At graded increasing continuous infusions, doses of drug yielded data as to ranges of administration rates required to achieve differing blood pressure responses.

Following these studies a set of preliminary acute open loop experiments (dogs 3'-8) were carried out to simulate by manual control the change of pressure which was desired to be achieved eventually by automated control. Mean spontaneous pressure was raised from 120-140 mm Hg to 180-200 mm Hg by constant intravenous infusion of NE (0.4-0.8 ug $kg^{-1}$ $min^{-1}$). After the blood pressure change plateau was maintained for 3 minutes (simulated hypertension) NP was infused at constant rates, and was increased stepwise to achieve the desired reduction in pressure. Infusion rates usually ranged from 10-25 ug $kg^{-1}min^{-1}$.

A prototype controller was then designed utilizing data gathered during these preliminary experiments. Controller function was tested on animal 9; revisions were included for animal 10. The experimental procedure for dogs 9-24 consisted of the same range of continuous NE infusion. However, manual control was superseded by closed loop automatic control with NP infusion (800 ug $ml^{-1}$ at maximum infusion rate of 1.9 cc $min^{-1}$) being determined by the apparatus of the invention. Modification of this procedure occurred in two cases where an attempt was made to increase blood pressure. In dog 12, both angiotensin II and NE were used as the hypertensive controlling agent. In dog 13 only NE was used by this device to achieve a preset desired level above the animal's spontaneous pressure.

Table 1 contains a summary of all experiments performed, the date, type of investigation or procedure, result and comments.

TABLE 1

This table is a summary of the historical progression involving animals for the development and testing of this device. Included are the dog numbers, date of experiment, type of procedure: bolus or impulse injection of drugs; continuous (cont.) infusion of drugs; controlled (ol) open loop or manual control without the invention in use; controlled (hyper) hypertension, the invention used to control a pressure above the spontaneous level; controlled hypotension (hypo), the invention used to control 2 pressure below the spontaneous level. Comments relative to the experiment indicate problem areas or improvements made in the procedure.

| Dog # | Date | Procedure | Comments |
|---|---|---|---|
| P | 4-25-73 | Harvard App. system test | Harvard App. Sys. not capable of closed loop control (± 30 mm Hg oscillation; 40 mm Hg overshoot) |
| 1 | 7-23-73 | bolus NE, NP cont. NE, NP | recording calibration in error; data not used |
| 2 | 7-24-73 | bolus NE, NP cont. NE, NP | Data used to derive design parameters |
| 3 | 8-6-73 | bolus NE, NP cont. NE, NP | Data used to derive design parameters |
| 3' | 8-7-73 | controlled (ol) hyper & hypo | NE used was old; results not valid, same animal as #3 |
| 4 | 8-14-73 | controlled (ol) hyper & hypo | results not valid; animal had cardiovascular disease |
| 5 | 8-16-73 | bolus NE, NP controlled (ol) hyper & hypo | data usd to derive design parameters |
| 6 | 8-20-73 | bolus NE, NP controlled (ol) hyper & hypo hemorrhage | data used to derive design parameters |
| 7 | 8-21-73 | bolus NE, NP controlled (ol) hyper & hypo | poor data |
| 8 | 8-22-73 | bolus NE, NP cont. NE, NP | exp. to see long term effects of NE & NP |
| 9 | 12-6-73 | test of controller prototype | electronic problems; need for redesign of diode and elimination of noise, 60 cycle and higher frequencies |
| 10 | 1-30-74 | later version of controller | settings were adjusted for proportional and derivative control |
| 11 | 3-5-74 | controlled hypotension | useable data |
| 12 | 3-13-74 | controlled: hypertension w/NE & Angiotensin II hypo w/NP | poor study; NP may have decayed in light |
| 13 | 4-2-74 | volume loaded controlled w/NP; hemorrhage controlled w/NE | attempt to simulate hypertension by increasing blood volume, not successful; hemorrhage used to produce shock model |
| 14 | 6-20-74 | controlld hypotension data obtained for | controller parameter proportional derivative amp. settings |
| 15 | 6-26-74 | controlled hypotension | same as 14 |
| 16 | 6-27-74 | controlled hypotension | same as 14 |
| 17 | 7-24-74 | controlled hypotension | same as 14; alternate filter attempted to reduce respiration effects; mild system oscillations resulted |
| 18 | 7-31-74 | controlled hypotension | same as 14; consistently good results with (animals 18-24) pump gearing setting 1.91 cc $min^{-1}$; prop. pot. = 4.0 der. pot. = 3.5 |
| 19 | 8-7-74 | controlled hypotension | same as 14; comparison made of performance between Harvard system and applicant's system same starting and desired pressure level used |
| 20 | 8-8-74 | controlled hypotension | same as 14; respiratory effects (spontaneous valsalva) reduced with deeper anesthesia |
| 21 | 11-12-74 | controlled hypotension | same as 14; drug indomethacin used to reduce tachphylaxis of NE; results fair |
| 22 | 11-14-74 | controlled hypotension | same as 21; animal underventilated; results fair |
| 23 | 12-5-74 | controlled hypotension | same as 19; indomethacin usd compared Harvard and applicant's systems |
| 24 | 2-6-75 | controlled hypotension | same as 18; various drug concentrations used to observe system onset delay times |

TOTAL 24 animals

INSTRUMENTATION

All data presented here was monitored by a Statham P23db transducer excited by a Honeywell Accudata 113 Bridge/D.C. amplifier. A filtered blood pressure signal (0.08 Hz cutoff, 0.0-2.0 V.D.C.) was sent to the Honeywell Oscillographic Recorder (model 1508-A). An unfiltered signal (0.0-10. V.D.C.) passes to the controller. The output from the controller is also recorded by the oscillograph and is sent to the Harvard Servo Amplifier (model 990). This amplifier, operating in mode B will be responsive to the drive signal provided by the controller (0.0–1.0 V.D.C.) and it in turn will control the servo operation of the Harvard pump (model 1991) for the infusion of drugs. Calibration for the recording apparatus was performed according to standard procedures outlined by the manufacturer.

CONTROLLER PARAMETER ADJUSTMENT PROCEDURE (1) Before infusion, the desired blood pressure reference level is set using the pot indicated for this purpose. The proportional control parameter is minimized at setting 9.1 (Table 2). Derivative control should be maximized at pot setting 1.0.

(2) After the subject has reached an induced or spontaneous blood pressure level, the titration of the pressure to the desired level is achieved by activating the controller. Activation is accomplished by positioning the blood pressure direction switch in the direction of desired titration.

Observations of the blood pressure course will indicate three results: (a) the desired blood pressure level is achieved, thus no further manipulation is necessary; (b) the pressure might overshoot and return to the desired level or to some steady state error; or (c) the system will not reach the desired level. If the overshoot is sustained, the explanation is physiologic, since the device automatically discontinues infusion once an overshoot has occurred, and the time course of drug effect is so short that the blood pressure rises rapidly to spontaneous levels within 2–3 minutes. Thus, sustained hypotension reflects a change in the intrinsic status of the subject.

(3) If (b) occurs with excessive overshoot, the pump gear setting should be reduced since maximum derivative control is already employed. If the overshoot is followed by a steady state error, with pressure in excess of the desired level, the pumping rate may be gradually increased by use of the proportional pot until this error is reduced to an acceptable level, but does not force the pressure to overshoot.

(4) If (c) results, the proportional pot is used to increase amplification until an acceptable error is achieved. If the maximum range of this control is used without achieving an acceptable value this condition reflects inadequate delivery of drug at maximal pumping rate. Therefore, it is necessary to reset the pump gear ratio to a higher maximal pumping rate and to readjust the proportional control. An alternative approach would require replacement of the drug solution with one of higher concentration.

(5) When maximum derivative control is in force, the system is extremely sensitive to rapid pressure changes induced by pulse pressure and changes in pressure induced by respiration. In some instances, where very little drug is required to maintain a desired pressure, this large derivative influence may bring steady state pressures beyond the desired. Reduction of the derivative influence is indicated.

TABLE 2

Proportional and derivative control potentiometer settings and the corresponding amplification factor.

| Proportional Pot. | | Derivative Pot. | |
| --- | --- | --- | --- |
| Pot Setting | Amplification | Pot Setting | Amplification |
| | | | (relative to Pot = 10) |
| 9.10 | 1:1 | 10 | 1:1 |
| 4.10 | 2:1 | 9 | 1:1 |
| 2.30 | 3:1 | 8 | 1.05:1 |
| 1.45 | 4:1 | 7 | 1.16:1 |
| 1.00 | 5:1 | 6 | 1.30:1 |
| .60 | 6:1 | 5 | 1.41:1 |
| .40 | 7:1 | 4 | 1.64:1 |
| .20 | 8:1 | 3 | 2.04:1 |
| | | 2 | 2.80:1 |
| | | 1 | 3.60:1 |

This procedure was tested on five animals, Table 1, #9–13 with varying degrees of success. In early trials, there were problems with reverse polarity after the desired pressure had been reached and the pump would consequently reverse. The mere placing of a diode in the circuit did not eliminate this problem for even germanium diodes require 0.2v turn on. These low voltages are in the operating range of the system. Therefore a modification was required which resulted in the use of a precision diode. Subsequently all oscillations due to this fault were eliminated.

RESULTS a. Controlled Hypotensive Models Using NP (1) With NE as the Hypertensive Agent When some steady state hypertensive condition is reached with NE, NP is infused through the use of the apparatus of this invention in the appropriate amount required to reach some desired level. Table 3 contains summary of the various attempts to maintain a constant pressure of 120 mm Hg. While the NE pump rate remains constant throughout the experiment, NP pump rates vary by an amount determined by the proportional and derivative control elements of the process of this invention. Two columns are of particular interest — overshoot and steady state error. For both, the desired level is zero. However, proportional and derivative control theory dictates that some steady state error may exist and be acceptable. The magnitude of this error depends upon its use; for clinical purposes we have determined ± 5 mm Hg desirable, but acceptable levels may range to ± 10 mm Hg.

Figure 4:
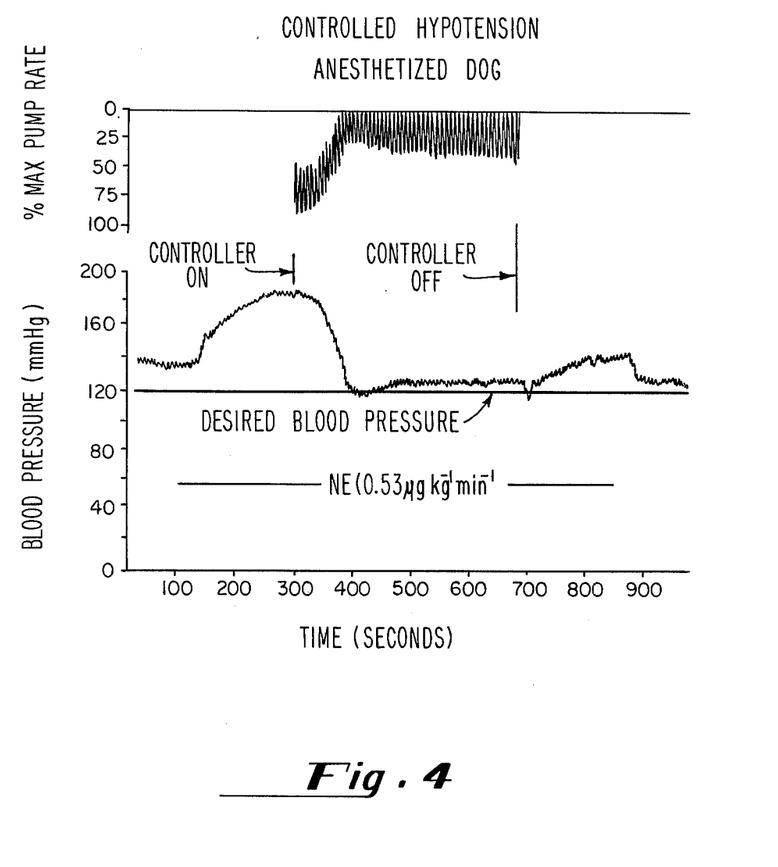
FIG. 4 is a graphic representation of the results of a controlled hypotension experiment using the apparatus and method of this invention to lower pressure.

After some period of trial and error in dog models reproducible settings were obtained for NP (800 ug/ml) which correspond to 5 on the Harvard pump (1.91 cc/min max). The proportional setting of 4.0 and derivative of 3.5 correspond to an amplification factor of 2:1 and 1.8:1 respectively. For example, in an experimental use of the process and apparatus of this invention (FIG. 4), the dog's aortic pressure was raised from a spontaneous mean value of 140 mm Hg to a plateau of 190 mm Hg by the constant infusion of NE. The controller was then activated to infuse nitroprusside to reduce the blood pressure to 120 mm Hg, represented by the lower curve. The upper curve represents the controller voltage output to the pump, with downward deflection representing increasing pumping rate. Incomplete filtering of the respiratory effects and pulse pressure is sensed by the derivative and results in pulsatile pumping. Note that in approximately two minutes, the desired level is reached. Full attenuation of these pressures would require a longer sampling period resulting in additional delays in response time and less acute control.

TABLE 3

This table indicates the effects of controlled infusion of NP (using the invention) to reduce a simulated hypertensive blood pressure (b.p. start) induced by continuous infusion of NE, to a desired level (P*). Letters following the dog number indicate separate segments of the experiment. Time to desired blood pressure level is the time from when the pressure begins its change until it reaches the desired level or some steady state (s.s. error) pressure. NE and NP pump setting numbers correspond to pump gear settings, where lower numbers indicate increased pump rates. Proportional (prop.) and derivative (der.) pot settings correspond to amplification factors contained in Table 2. Comments relative to the experiment indicate problem areas or improvements made in the procedure.

Additional animal experiments not included in Table 3, but summarized in Table 1 (dogs 14-24) indicate that the parameter settings used above were generally applicable to canine subjects.

(2) With Angiotensin II as a Hypertensive Agent

Angiotensin II was only used for one model in animal #12. From previous discussions concerning the pharmacodynamics of these agents, angiotensin was found to have approximately the same pressure inducing effect as NE, as shown in Table 4:

TABLE 4

This table indicates the effects of controlled infusion of NP to reduce a simulated hypertensive blood pressure (b.p. start) induced by continuous infusion of angiotensin II, to a desired level (P*). Letters following the dog number indicate separate segments of the experiment. Time to desired blood pressure level is the time from when the pressure begins its change until it reaches the desired level or some steady state (s.s. error) pressure. NE and NP pump setting numbers correspond to pump gear settings, where lower numbers indicate increased pump rates. Proportional (prop.) and derivative (der.) pot settings correspond to amplification factors contained in Table 2. Comments relative to the experiment indicate problem areas or improvements made in the procedure.

TABLE 5

This table indicates the effects of controlled infusion of NE (using the invention) to increase blood pressure in a dog from a spontaneous blood pressure (b.p. start) to some hypertensive state (P*). Letters following the dog number indicate separate segments of the experiment. Time to desired blood pressure level is the time from when the pressure begins its change until it reaches the desired level or some steady state (s.s. error) pressure. NE and NP pump setting numbers correspond to pump gear settings, where lower numbers indicate increased pump rates. Proportional (prop.) and derivative (der.) pot settings correspond to amplification factors contained in Table 2. Comments relative to the experiment indicate problem areas or improvements made in the procedure.

TABLE 3

| Dog # | b.p. start (mm Hg) | P* (mm Hg) | Time desired (sec.) | NE pump setting | NP pump setting | overshoot (mmHg) | s.s. error (mmHg) | prop. setting | der. setting | Comment |
|---|---|---|---|---|---|---|---|---|---|---|
| 10-C | 160 | 100 | — | — | 2 | 20 | 20 | 8.2 | 4.5 | s.s. error excessive; required more gain |
| D | 155 | 120 | — | — | 2 | 25 | 0 | " | " | |
| E | 160 | 120 | — | — | 3 | 10 | 15 | " | " | still requires finer control |
| 11-A | 180 | 120 | 50 | 11 | 2 | 40 | — | 7.6 | 4.5 | too much overshoot; der. should be increased |
| B | 170 | 120 | 60 | 11 | 3 | 20 | — | " | " | |
| C | 170 | 120 | — | 11 | 4 | 15 | — | " | " | |
| D | 165 | 120 | 110 | 11 | 5 | 10 | — | " | " | |
| E | 180 | 120 | — | 11 | 6 | — | ±15 | " | " | slow osc; need more gain |
| F | 170 | 120 | — | 10 | 5 | 0 | 15 | 3.0 | 4.5 | |
| G | 170 | 120 | 120 | 11 | 5 | 10 | 10 | 4.0 | 4.5 | |
| H | 175 | 120 | 60 | 10 | 5 | 12 | 0 | 4.0 | 3.0 | acceptable |
| I | 165 | 120 | 50 | 9 | 5 | 10 | 0 | " | " | |
| I' | 170 | 120 | 80 | 9 | 5 | 15 | 0 | " | " | |
| 12-D | 200 | 120 | 80 | 13 | 5 | — | 10 | 4.0 | 3.0 | needs more gain |
| E | 180 | 120 | 40 | 13 | 4 | — | 10 | 3.0 | 4.0 | |
| F | 165 | 120 | 70 | 13 | 4 | 0 | 2 | " | " | acceptable |
| 13-D | 200 | 120 | 80 | 11 | 5 | 5 | 5 | 4.0 | 3.5 | |
| E | 200 | 120 | 80 | 11 | 5 | 5 | 0 | " | " | animal off respirator |
| F | 190 | 120 | 80 | 10 | 5 | 0 | 0 | " | " | animal off respirator |

TABLE 4

| Dog # | b.p. start (mm Hg) | P* (mm Hg) | Time desired (sec.) | NE pump setting | NP pump setting | overshoot (mmHg) | s.s. error (mmHg) | prop. setting | der. setting | Comment |
|---|---|---|---|---|---|---|---|---|---|---|
| 12-G | 185 | 120 | 120 | 14 | 4 | — | 15 | 3.0 | 3.0 | requires more again |
| H | 160 | 120 | 90 | 12 | 3 | — | 0 | 2.5 | 3.0 | |
| I | 155 | 120 | 70 | 10 | 3 | 0 | 0 | 3.0 | 3.5 | reasonable setting |
| J | 160 | 120 | 100 | 10 | 3 | 0 | 0 | 3.0 | 3.5 | reasonable setting |

TABLE 5

| Dog # | b.p. start (mmHg) | P* (mmHg) | Time desired (sec.) | NE pump setting | NP pump setting | over-shoot (mmHg) | s.s. error (mmHg) | prop. setting | der. setting | Comment |
|---|---|---|---|---|---|---|---|---|---|---|
| 10-A | 150 | 180 | — | 3 | 0 | — | 15 | 8.1 | 4.5 | s.s. error large, requires more gain |
| B | 140 | 180 | — | 2 | 0 | — | 5 | 8.1 | 4.5 | derivative control could be increased | b. Controlled Hypertension using Norepinerphrine
(1) Without any Hypotensive Agent The pressor effects of norepinephrine demonstrate similar constants to nitroprusside. Therefore, it is logical that the apparatus of this invention would be capable of raising a pressure to some desired level using similar derivative and proportional settings, but by reversing the direction of desired blood titration. After changing the blood pressure direction switch on the controller to raise blood pressure, dog 10-A, B (Table 5) was used in this test. This animal had a spontaneous pressure of 140–150 mm Hg. The desired blood pressure level was set for 180 mm Hg. The controller, utilizing the same theory as described previously, was activated and the system raised the animal's pressure to within 5 mm Hg of the desired pressure. This indicates the feasibility for operation of the apparatus of the invention to raise pressures with rapidly acting vasopressor agents.

We claim:

1. Apparatus for infusing drugs into a patient to achieve a desired blood pressure level comprising:
    means for developing a representation of said desired level;
    transducer means for evaluating the present blood pressure of the subject, and for developing a signal in correspondence therewith;
    control means, responsive to the difference between said representation of said desired pressure and the signal in correspondence with said present pressure, and to the derivative of said difference, for developing an infusion control signal; and
    pump means, responsive to said infusion control signal, for injecting said drugs into the patient.

2. Apparatus for infusing drugs into a patient to achieve a desired blood pressure level comprising:
    means for developing a representation of said desired level;
    transducer means for evaluating the present blood pressure of the subject, and for developing a signal in correspondence therewith;
    control means, responsive to the difference between said representation of said desired pressure and the signal in correspondence with said present pressure, and to the derivative of said difference, for developing an infusion control signal;
    pump means, responsive to said infusion control signal, for injecting said drugs into the subject; and
    wherein said transducer means includes filter means for developing a signal representative of mean arterial pressure, said control means operating responsively to the difference between said representation of said desired pressure and said signal representative of mean arterial pressure, and to the derivative of said difference between said representation of said desired pressure and said signal representative of said mean arterial pressure.

3. Apparatus as described in claim 2, wherein said filter means includes means for integrating the evaluated present blood pressure from said transducer.

4. Apparatus for infusing drugs into a patient to achieve a desired blood pressure level comprising:
    transducer means for evaluating the present blood pressure of the subject;
    control means, responsive to the difference between said desired pressure and said present pressure, and to the derivative of said difference, for developing an infusion control signal; and
    pump means, responsive to said infusion control signal, for injecting said drugs into the subject;
    wherein said control means comprises means for developing a reference signal corresponding to said desired pressure level;
    means for developing an error signal between said reference signal and a signal from said transducer means repesentative of present blood pressure;
    means for scaling said error signal by a predetermined factor;
    means for evaluating the rate of change of said error signal; and
    said pump means being responsive to said rate of change and to the scaled error signal.

5. Apparatus as described in claim 4 wherein said control means further includes means for combining and for amplitude scaling the combination of said rate of change and said scaled error signal.

6. In a closed loop drug infusion system for controlling a subject's measured blood pressure to a specified desired pressure, an improvement comprising:
    means for developing measured pressure and the desired pressure;
    means for integrating measured blood pressure to mean arterial pressure;
    means for comparing said mean arterial pressure with the desired pressure, control being based on the results of said comparing; and
    control means, responsive to said means for comparing, for regulating drug infusion based on a proportional plus derivative control mode.

7. A method of controlling infusion of drugs into a subject to bring present blood pressure to a desired pressure level comprising the steps of:
    evaluating said present pressure and said desired pressure;
    evaluating the error between the present pressure and the desired pressure;
    developing a control signal based on said error and on the time rate of change of said error; and
    regulating the infusion of drugs in response to changes in said control signal.

8. A method of controlling infusion of drugs into a subject to bring present blood pressure to a desired pressure level comprising the steps of:
    evaluating said present pressure and said desired pressure;
    evaluating the error between the present pressure and the desired pressure;
    developing a control signal based on said error and on the time rate of change of said error;

regulating the infusion of drugs in response to changes in said control signal;

sensing the present blood pressure of the subject;

filtering the sensed present pressure to produce a representation of mean arterial pressure; and comparing said representation with the desired pressure level, thereby producing a signal representative of said error.

9. A method as described in claim 8 wherein said filtering step includes integrating the sensed present pressure.

10. The method of controlling the blood pressure of a mammal which comprises the steps of:

(a) establishing a certain desired blood pressure;

(b) continuously sensing the mean arterial blood pressure of said mammal;

(c) continuously evaluating the difference between sensed mean arterial blood pressure and said desired pressure;

(d) continuously administering intravenously a drug effective to alter said mammal's blood pressure in response to said difference in accordance with the following control relationship, $$\text{control} = A \times \text{difference} + B \times \frac{d(\text{difference})}{dt},$$

where A and B are predetermined scaling factors.

* * * * *

UNITED STATES PATENT OFFICE
CERTIFICATE OF CORRECTION

Patent No. 4,080,966            Dated March 28, 1978

Inventor(s) Robert T. McNally, Karl Engelman, Abraham Noordergraaf

It is certified that error appears in the above-identified patent and that said Letters Patent are hereby corrected as shown below:

In Table 1, column 10, the data for Dog #14 should appear as follows:

14    6-20-74    controlled hypotension    controller parameter data obtained for proportional derivative amp. settings Column 15, line 10, "Norepinerphrine" should be --Norepinephrine--.

Signed and Sealed this

Twenty-second Day of August 1978

[SEAL]

Attest:

RUTH C. MASON
Attesting Officer

DONALD W. BANNER
Commissioner of Patents and Trademarks